US 8,165,378 B2

United States Patent
Fritz et al.

(10) Patent No.: US 8,165,378 B2
(45) Date of Patent: Apr. 24, 2012

(54) METHOD AND APPARATUS FOR VISUALIZING TUBULAR ANATOMICAL STRUCTURES, IN PARTICULAR VESSEL STRUCTURES, IN MEDICAL 3D IMAGE RECORDS

(75) Inventors: Dominik Fritz, Karlsruhe (DE); Michael Scheuering, Nürnberg (DE); Johann Uebler, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 418 days.

(21) Appl. No.: 12/453,950

(22) Filed: May 28, 2009

(65) Prior Publication Data
US 2009/0297010 A1 Dec. 3, 2009

(30) Foreign Application Priority Data

May 28, 2008 (DE) .................. 10 2008 025 537
Mar. 25, 2009 (DE) .................. 10 2009 014 764

(51) Int. Cl.
*G06K 9/00* (2006.01)
*A61B 5/05* (2006.01)
(52) U.S. Cl. ........ 382/131; 382/128; 382/132; 600/407; 600/410
(58) Field of Classification Search .......... 382/128–132; 600/407, 410, 425
See application file for complete search history.

(56) References Cited

U.S. PATENT DOCUMENTS

| | | | | |
|---|---|---|---|---|
| 6,643,533 B2 * | 11/2003 | Knoplioch et al. | ............ | 600/407 |
| 6,718,193 B2 * | 4/2004 | Knoplioch et al. | ............ | 600/407 |
| 7,200,251 B2 * | 4/2007 | Joshi et al. | .................... | 382/128 |
| 7,379,062 B2 * | 5/2008 | Poole | ............................ | 345/424 |
| 7,623,900 B2 * | 11/2009 | Graham et al. | ............... | 600/407 |
| 7,787,683 B2 * | 8/2010 | Khamene et al. | ............. | 382/130 |
| 7,825,924 B2 * | 11/2010 | Matsumoto | .................... | 345/419 |
| 2002/0118869 A1 | 8/2002 | Knoplioch et al. | | |
| 2002/0176614 A1 | 11/2002 | Kuth et al. | | |

FOREIGN PATENT DOCUMENTS
DE    10119454 A1    10/2002

OTHER PUBLICATIONS

Office Action issued on Jun. 8, 2011 in corresponding German Patent Application No. 10 2009 014 764.0.

* cited by examiner

*Primary Examiner* — Sang Nguyen
(74) *Attorney, Agent, or Firm* — Harness, Dickey & Pierce, P.L.C.

(57) ABSTRACT

A method and an apparatus are disclosed for visualizing tubular anatomical structures, in particular vessel structures, in medical 3D image records. The method according to at least one embodiment of the invention includes: providing 3D image data of the tubular anatomical structure; determining a centerline of the tubular anatomical structure in the 3D image data; selecting a point of the centerline; generating a 2D slice image assigned to the point, the 2D slice image representing a sectional plane in the 3D image data, which sectional plane is arranged relative to a section of the centerline, including the point and a prescribable section start point and section end point of the section, such that an orthogonal distance from the sectional plane for each centerline point of the section is less than or equal to a prescribed value R, the value R being selected to be greater than a value $R_{krit}$, and $R_{krit}$ specifying the value for which precisely one such sectional plane can be determined; and visually displaying the 2D slice image.

26 Claims, 2 Drawing Sheets

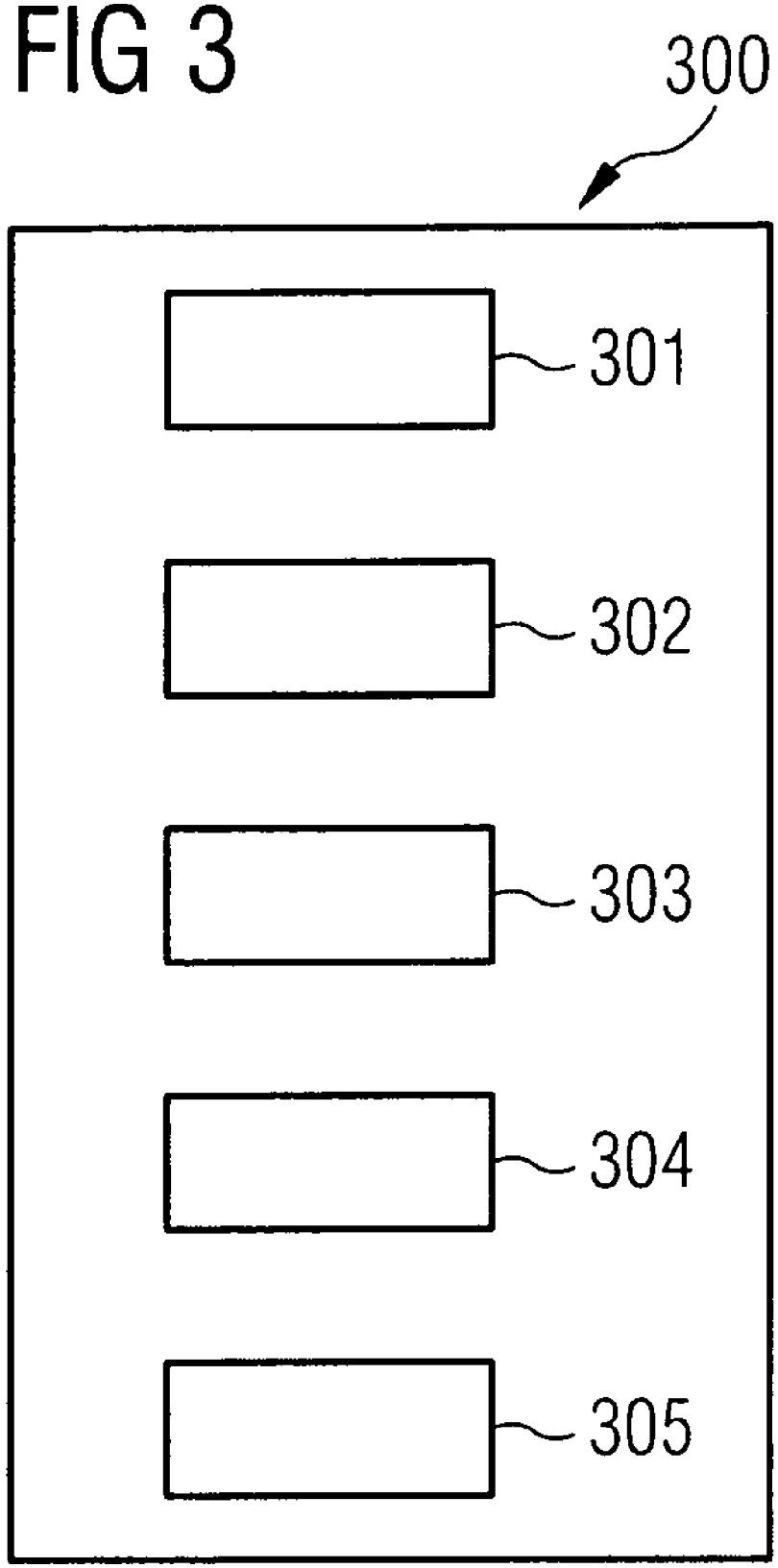

METHOD AND APPARATUS FOR VISUALIZING TUBULAR ANATOMICAL STRUCTURES, IN PARTICULAR VESSEL STRUCTURES, IN MEDICAL 3D IMAGE RECORDS

PRIORITY STATEMENT

The present application hereby claims priority under 35 U.S.C. §119 on German patent application numbers DE 10 2008 025 537.8 filed May 28, 2008, and DE 10 2009 014 764.0 filed Mar. 25, 2009, the entire contents of each of which are hereby incorporated herein by reference.

The present application is generally related to an application entitled "METHOD FOR VISUALIZING TUBULAR ANATOMICAL STRUCTURES, IN PARTICULAR VESSEL STRUCTURES, IN MEDICAL 3D IMAGE RECORDS" filed in the USPTO on the same date as the present application and claiming priority to German patent application number DE 10 2008 025 535.1 filed May 28, 2008, the entire contents of which is hereby incorporated herein by reference.

FIELD

At least one embodiment of the present invention is in the field of medical technology and generally relates to a method and/or an apparatus for visualizing tubular anatomical structures, in particular vessel structures, in medical 3D image records. In at least one embodiment, such 3D image records, or corresponding 3D image data, can be obtained using known medical imaging techniques, such as computed tomography, nuclear magnetic resonance imaging (NMRI), magnetic resonance imaging (MRI) or sonography. Here, a stack of 2D slice image records of an examination object is typically generated and the stack overall constitutes the 3D image record.

BACKGROUND

These days, medical 3D image records are predominantly evaluated using visually displayed 2D slice images which are generated on the basis of the recorded 3D image data. This practice is also applied if the structures to be analyzed in the 3D image records have a tubular geometry. Examples of tubular structures include tubular hollow organs, such as the colon, or vessels, such as e.g. the aorta or the coronary vessels. In the latter cases, the evaluation of the tubular structures is particularly focused on analyzing pathological changes, usually on the inner walls of the tubular structure. A stenotic region in a vessel section is mentioned here in an exemplary manner. From a medical point of view, it is the goal in this case to find out to what extent the narrowed region influences the overall medical function of the vessel section. In the present example of narrowing of vessels, this means that the medical practitioner analyzes the 3D image records to determine whether enough blood can still flow through the vessel, despite the narrowing of the vessel, so that e.g. the myocardium still has a sufficient supply of oxygen.

For the evaluation of tubular structures, the prior art discloses the determination of a centerline in the recorded 3D image data, which centerline represents the three-dimensional tubular structure imaged in the 3D image data. To this end, the prior art uses known skeletonizing or thinning methods. Here, this centerline is used as a path for the visualization using 2D slice images. This means that for a point of the centerline which can be selected manually (every image voxel belonging to the centerline), one 2D cross section of the tubular structure, which is orthogonal to the centerline at the selected point, and two 2D slice images with tangential sectional planes are generally calculated and displayed visually. Usually, all three planes are orthogonal to one another. By repeatedly selecting points of the centerline, corresponding 2D slice images, respectively containing the selected point, are generated and displayed. Particularly when continuously selecting adjacent points of the centerline, corresponding to, for example, continuous motion back and forth along the path, the tubular structure can be evaluated using the 2D slice images respectively displayed in the process.

However, the problem with this procedure is that, particularly in the case of strongly curved tubular structures or else in the case of tubular structures whose curvature changes weakly but frequently, the described 2D slice images (tangential planes) "jump" very strongly from image to image when "continuously passing over the path". Hence, the display profile when continuously passing over the structure is very jittery; this requires the increased attention of the evaluating medical practitioner and increases the risk of misinterpretation of the displayed 2D slice images.

SUMMARY

In at least one embodiment of the invention, at least one of a method and an apparatus are specified for visualizing tubular anatomical structures, in particular vessel structures, in medical 3D image records in which the problems described above are avoided and a faster and more reliable evaluation of tubular anatomical structures is made possible.

According to at least one embodiment of the invention, the method for visualizing tubular anatomical structures, in particular vessel structures, in medical 3D image records comprises the following steps:

Step a):
Providing 3D image data of the tubular anatomical structure. Here, the 3D image data was typically produced using a medical imaging method, such as computed tomography, nuclear magnetic resonance imaging, magnetic resonance imaging or sonography. In principle, the method can be applied to all 3D image data in which tubular structures intended to be examined are imaged.

Step b):
Determining a centerline of the tubular anatomical structure in the 3D image data. To this end, the prior art discloses applicable methods. Advantageously, the centerline is determined by skeletonizing or thinning the 3D image data. In a particularly preferred manner, the centerline is determined by segmenting and subsequent skeletonizing of the 3D image data.

Step c):
Selecting a point P of the centerline. The point P can be selected automatically or preferably by a manual input from an operator. In the latter case, the centerline, which was previously determined in the 3D image data, is preferably displayed visually. Hence, the operator can interactively select the point P on the centerline of the tubular structure. The operator preferably selects the point P using an input unit such as a computer mouse, a keyboard, a voice control unit, etc.

Step d):
Generating a 2D slice image assigned to the point P. Here, the 2D slice image generated in the process represents a sectional plane in the 3D image data, which sectional plane is arranged relative to a section of the centerline, comprising the point P and a prescribable section start point and section end point of the section, such that an orthogonal distance from the sectional plane for each centerline point of the section is less than or equal to a prescribed value R. In this context, reference is made to the fact that in this document an orthogonal distance is understood to be a distance which is perpendicular to the sectional plane. According to the invention, the value of R is selected to be greater than a value $R_{krit}$, $R_{krit}$ specifying the value of R for which precisely one such sectional plane in accordance with the abovementioned conditions can be determined. (NB: If R is less than $R_{krit}$, no sectional plane can be determined which satisfies the specified conditions.)

In a particularly advantageous manner, the value R is selected such that R is less than or equal to the maximum cross-sectional radius of the tubular structure along the section, in particular such that R is less than or equal to half of this maximum cross-sectional radius. It goes with out saying that in this case R is always greater than $R_{krit}$. This ensures that the 2D slice image runs within the tubular structure along the observed section of the centerline, and thus, in particular, an optimal evaluation of inner vessel walls, for example, is possible.

Hence, in this method step d), a section (part) of the centerline is first of all prescribed by fixing a section start point and a section end point on the centerline. The following advantageous embodiments of the method are used to fix (prescribe) the section.

The section start point and/or the section end point can be fixed or prescribed manually by an operator or automatically as a function of the point P. In a particularly advantageous manner, the section start point and the section end point are prescribed such that, along the centerline, the point P is equidistant from the section start point and the section end point. In an alternative embodiment, the section start point and/or the section end point are automatically prescribed as a function of the selection of the point P and the values of R and $R_{krit}$. If the centerline has a large curvature, the section start point and/or the section end point, for example, are changed as a function of the point P such that, as a result of this, the length of the section is reduced until a sectional plane can be specified for the given R under the conditions according to the invention specified above.

In an alternative embodiment, the section start point or the section end point is identical to the point P. Furthermore, the distance between the section start point and section end point along the centerline can advantageously be prescribed as a function of the maximum cross-sectional radius of the tubular structure along the centerline. In a particularly advantageous manner, 5 to 50 times, advantageously 20 times, in particular 10 times the maximum cross-sectional radius of the tubular structure along the centerline is prescribed as the distance along the centerline between the section start point and the section end point.

Step e):
Visually displaying the 2D slice image generated. This is typically effected on a monitor or a screen. It goes without saying that further display device(s) known to the person skilled in the art are suitable to this end.

In addition to the distance-dependent determination of a 2D slice image described above in step d), the three dimensional orientation of the sectional plane of the 2D slice image is advantageously fixed by a principal component analysis of all centerline points of the section. In the process, the 3D orientation of the sectional plane is defined by those two vectors, obtained as the result of the principal component analysis, which represent the largest and second-largest spatial variance of the centerline points of the section.

Alternatively or additionally, the 3D orientation of the sectional plane in step d) can be fixed by way of a quality measure dependent optimization method. In the process, the quality measure can comprise one or more parameters. Thus, in a first embodiment variant, the quality measure is the number of the centerline points of the section whose orthogonal distance from the sectional plane is less than a prescribable value r, with $R_{krit}<r<R$. Applied to the 3D image data, the number of these centerline points corresponds to a corresponding number of image voxels which represent the section of the centerline in the 3D image data.

In a particularly advantageous embodiment variant, the method is again repeatedly run through after step e), starting with step c). In particular, this makes a continuous visualization of the tubular structure along the centerline generated in step b) possible, without the occurrence of a "jump" or fast directional changes between the 2D slice images displayed in step e).

In a further embodiment variant, a quality measure dependent optimization method for determining a 3D orientation of the sectional plane 1 is carried out in step d), in which an angle α between a first normal of a 2D sectional plane and a second normal of a 2D sectional plane is used as a quality measure, the first normal of a 2D sectional plane relating to a first 2D slice image already displayed in step e) and the second normal of a 2D sectional plane relating to a second 2D slice image with a second 2D sectional plane, generated in a step d) following the step e), and the 3D orientation of the second sectional plane being determined such that the angle α is minimized.

In addition to the 2D slice image generated according to at least one embodiment of the invention and assigned to the point P, a 2D cross section assigned to the point P can additionally be generated in step d) and displayed in step e), the 2D cross section representing a sectional plane in the 3D image data which is aligned orthogonally with respect to the centerline of the tubular structure at the point P. Advantageously, two 2D slice images and a 2D cross section are generated for the point P in step d). A simple interpretability of the generated 2D slice images results if the previously mentioned two 2D slice images and the 2D cross section respectively have sectional planes in the 3D image data which are arranged orthogonally with respect to one another.

An advantage of at least one embodiment of the described method is that "jumping" between subsequent displays of 2D slice images and fast changes of direction are avoided in the case of an evaluation of the tubular anatomical structure along the centerline. At the same time, this results in an optimal display of the examined tubular structure. Overall, this makes a faster, less error prone, user friendly and hence more efficient evaluation possible.

According to at least one embodiment of the invention, the apparatus for visualizing tubular anatomical structures, in particular vessel structures, from medical 3D image records at least comprises the following units:
  a storage module which is used to store 3D image data of the tubular anatomical structure,
  a first module which is used to determine a centerline of the tubular anatomical structure based on the 3D image data,
  a second module which is used to select a point P on the centerline,
  a third module, which is used to generate a 2D slice image assigned to the point P from the 3D image data, the 2D slice image representing a sectional plane in the 3D image data, which sectional plane is arranged relative to a section of the centerline, comprising the point P and a prescribable section start point and section end point of the section, such that an orthogonal distance from the sectional plane for each centerline point of the section is less than or equal to a prescribed value R, the value of R being selected to be greater than a value $R_{krit}$, and $R_{krit}$ specifying the value of R for which precisely one such sectional plane can be determined, and a display unit which is used to visually display the 2D slice image assigned to the position P.

In one embodiment variant of the apparatus, the first module is designed such that the first module for determining the centerline can be used to segment and subsequently skeletonize the 3D image data.

In one embodiment variant of the apparatus, the second module is designed such that the point P can be selected by an operator. To this end, the second module can have an input unit or can be connected to such an input unit.

In a further embodiment variant of the apparatus, the third module is designed such that the section start point and/or the section end point can be selected by an operator. To this end, the third module can have an input unit or can be connected to such an input unit.

In a further example embodiment of the apparatus, the third module is designed such that the section start point and/or the section end point can be selected automatically as a function of the point P. To this end, the third module can have a computational unit. The third module is preferably designed such that the section start point and the section end point can be prescribed such that, along the centerline, the point P is equidistant from the section start point and the section end point. As an alternative to this, the third module is designed such that the section start point and the section end point can be prescribed such that the point P and either the section start point or the section end point are identical. In a particularly preferred further alternative embodiment of the apparatus, the third module is designed such that the distance between the section start point and the section end point along the centerline can be prescribed as a function of the maximum cross-sectional radius of the tubular structure along the section. In particular, the third module can be designed and set up such that the section start point and/or the section end point are automatically prescribed as a function of the point P and of the values of R and $R_{krit}$.

In a further embodiment of the apparatus according to the invention, the third module is designed such that a 2D cross section assigned to the point P can additionally be generated on the basis of the 3D image data, the 2D cross section in the 3D image data representing a sectional plane which, at the point P, is aligned orthogonally with respect to the centerline of the tubular anatomical structure.

BRIEF DESCRIPTION OF THE DRAWINGS

Example embodiments of the invention and further advantageous refinements of the invention are illustrated in the following schematic drawings, in which:

FIG. 3 shows a schematic design of an apparatus according to an embodiment of the invention.

DETAILED DESCRIPTION OF THE EXAMPLE EMBODIMENTS

Figure 1:
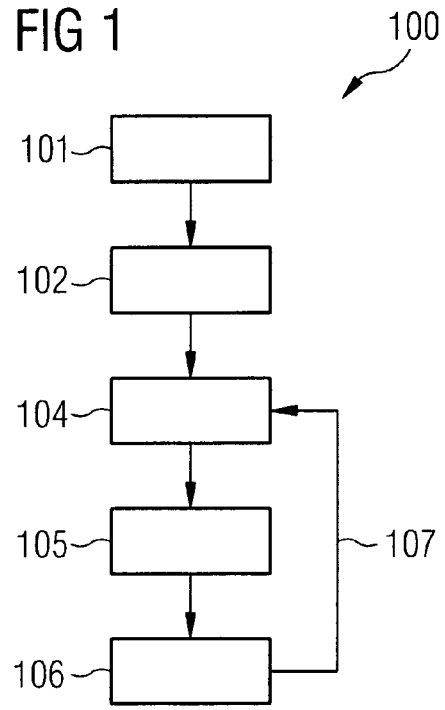
FIG. 1 shows a flowchart of the method according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 schematically shows the sequence of method steps of the method 100 according to an embodiment of the invention for visualizing tubular anatomical structures in medical 3D image records. 3D image data of the tubular anatomical structure is provided in step 101. A centerline 201 of the tubular anatomical structure in the 3D image data is determined in step 102. A point P of the centerline 201 is selected in step 104. A 2D slice image assigned to the point P is generated in step 105, the 2D slice image representing a sectional plane 205 in the 3D image data, which sectional plane is arranged relative to a section 208 of the centerline 201, comprising the point P and a prescribable section start point and section end point 203, 204 of the section 208, such that an orthogonal distance 207 from the sectional plane 205 for each centerline point of the section 208 is less than or equal to a prescribed value R. Here, the value of R is selected to be greater than a value $R_{krit}$, $R_{krit}$ specifying the value of R for which precisely one such sectional plane 205 can be determined. The 3D orientation of the sectional plane 205 is determined by a principal component analysis of all centerline points of the section 208, the 3D orientation being defined by those two vectors, obtained in the process, which represent the largest and second-largest spatial variance of the centerline points of the section 208. A sectional plane in the 3D image data can be determined unambiguously by prescribing the 3D orientation and the value R.

A visual display of the determined 2D slice image is effected in step 106. After the visual display of the 2D slice image, the method is carried out repeatedly, starting with step 104. The reference symbol 107 characterizes the repeating method sequence.

In a particularly preferred variant of an embodiment of the method, the point P is selected in method step 104 by a continuous migration along the section 208 of the centerline 201, with migration being possible in two directions. This "migrating along" the centerline 201 is preferably controlled or initiated by an operator by way of an input device such as a computer mouse, for example.

Figure 2:
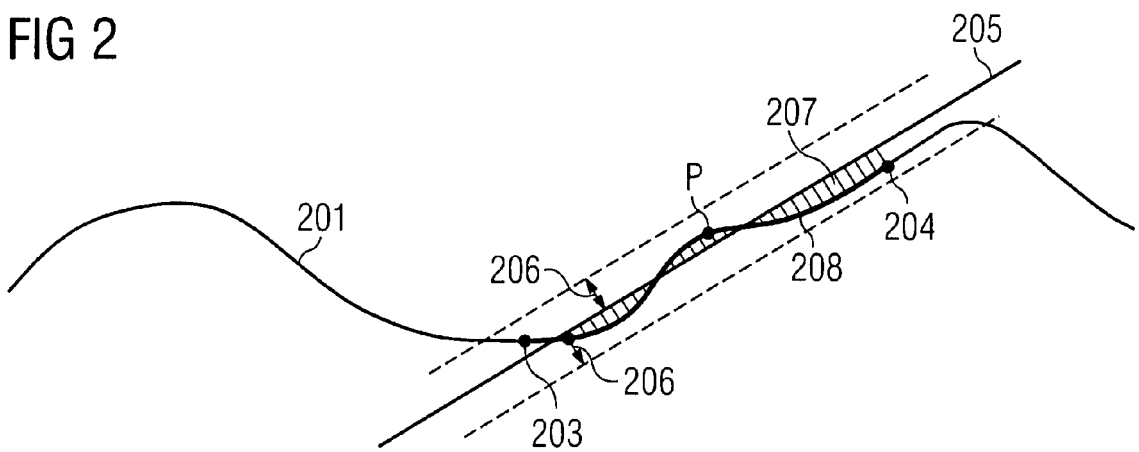
FIG. 2 shows a schematized 2D illustration of the centerline of the tubular structure determined in method step b) and a 2D sectional plane generated according to an embodiment of the invention.

FIG. 2 shows a schematized 2D illustration of the centerline 201 of the tubular structure determined in method step b) and a 2D sectional plane 205 generated according to an embodiment of the invention. Hence, the illustration shows the conditions after carrying out method step d). After skeletonizing/thinning, the tubular anatomical structure is represented by its centerline 201. The point P was selected on the centerline. The section start point and section end point 203, 204 were automatically selected such that, along the centerline 201, the point P is equidistant from the section start point and section end point 203, 204. The section 208 of the centerline 201 defined in this way is highlighted in the illustration by the centerline 201 having an increased line thickness. The dashed lines characterize the region in which the orthogonal distance between centerline points of the section 208 and the sectional plane 205 is less than or equal to a prescribed value R (reference symbol 206). The respective orthogonal distance between the centerline points of the section 208 and the sectional plane 205 is illustrated by the shaded regions 207 between the section 208 and the sectional plane 205.

FIG. 3 shows the schematic design of an apparatus 300 according to an embodiment of the invention for visualizing tubular anatomical structures in medical 3D image records. The apparatus comprises a storage module 301 which is used to store 3D image data of the tubular anatomical structure, a first module 302 which is used to determine a centerline 201 of the tubular anatomical structure based on the 3D image data, a second module 303 which is used to select a point P on the centerline 201, a third module 304, which is used to generate a 2D slice image assigned to the point (P) from the 3D image data, the 2D slice image representing a sectional plane 205 in the 3D image data, which sectional plane is arranged relative to a section 208 of the centerline 201, comprising the point P and a prescribable section start point and section end point 203, 204 of the section 208, such that an orthogonal distance 207 from the sectional plane 205 for each centerline point of the section 208 is less than or equal to a prescribed value R, and a display unit 305 which is used to visually display the 2D slice image assigned to the point P.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualizing tubular anatomical structures in medical 3D image records, comprising:
   providing 3D image data of a tubular anatomical structure;
   determining a centerline of the tubular anatomical structure in the 3D image data;
   selecting a point of the determined centerline;
   generating a 2D slice image assigned to the selected point, the 2D slice image representing a sectional plane in the 3D image data, the sectional plane being arranged relative to a section of the centerline, the section including the point, a prescribable section start point and a section end point of the section, such that an orthogonal distance from the sectional plane for each centerline point of the section is less than or equal to a prescribed value R, R being selected to be relatively greater than a value $R_{krit}$ and $R_{krit}$ specifying a value of R for which precisely one such sectional plane is determinable; and
   visually displaying the generated 2D slice image, wherein the generating a 2D slice image includes effecting a principal component analysis of all centerline points of the section to determine a 3D orientation of the sectional plane, the 3D orientation being defined by two vectors which represent a relatively largest and relatively second-largest spatial variance of the centerline points of the section.

2. A method for visualizing tubular anatomical structures in medical 3D image records, comprising:
   providing 3D image data of a tubular anatomical structure;
   determining a centerline of the tubular anatomical structure in the 3D image data;
   selecting a first point of the determined centerline;
   generating a first 2D slice image assigned to the first point, the 2D slice image representing a first sectional plane in the 3D image data, the first sectional plane being arranged relative to a first section of the centerline, the first section including the first point, a first prescribable section start point and a first section end point of the first section, such that an orthogonal distance from the first sectional plane for each centerline point of the first section is less than or equal to a first prescribed value R, the first value R being selected to be relatively greater than a first value $R_{krit}$ and the first value $R_{krit}$ specifying a value of the first value R for which precisely one such first sectional plane is determinable;
   visually displaying the generated first 2D slice image;
   generating a second 2D slice image assigned to a second selected point, the second 2D slice image representing a second sectional plane in the 3D image data; and
   performing a quality measure dependent optimization method for determining a 3D orientation of the second sectional plane, in which an angle $\alpha$ between a first normal of a first 2D sectional plane and a second normal of a second 2D sectional plane is used as a quality measure, the first normal of the first 2D sectional plane relating to the first 2D slice image displayed in the visually displaying the generated 2D slice image and the second normal of the second 2D sectional plane relating to the second 2D slice image with the second sectional plane,
   wherein the 3D orientation of the second sectional plane is determined such that the angle $\alpha$ is minimized.

3. The method as claimed in claim 2, further comprising:
   displaying the determined centerline before the selecting a first point.

4. The method as claimed in claim 3, further comprising:
   visually displaying the determined centerline after the visually displaying the second 2D slice image;
   selecting the second point of the determined centerline; and
   visually displaying the generated second 2D slice image;
   wherein the second sectional plane is arranged relative to a second section of the centerline, the second section including the second point, a second prescribable section start point and a second section end point of the second section, such that an orthogonal distance from the second sectional plane for each centerline point of the second section is less than or equal to a second prescribed value R, the second value R being selected to be relatively greater than a second value $R_{krit}$ and the second value $R_{krit}$ specifying a value of the second value R for which precisely one such second sectional plane is determinable.

5. A computer readable medium including program segments for, when executed on a computer device, causing the computer device to implement the method of claim 3.

6. The method as claimed in claim 2, further comprising:
   selecting the second point of the determined centerline; and
   visually displaying the second 2D slice image,
   wherein the second sectional plane is arranged relative to a second section of the centerline, the second section including the second point, a second prescribable section start point and a second section end point of the second section, such that an orthogonal distance from the second sectional plane for each centerline point of the second section is less than or equal to a second prescribed value R, the second value R being selected to be relatively greater than a second value $R_{krit}$ and the second value $R_{krit}$ specifying a value of the second value R for which precisely one such second sectional plane is determinable.

7. A computer readable medium including program segments for, when executed on a computer device, causing the computer device to implement the method of claim 6.

8. The method as claimed in claim 2, wherein the first section start point and the first section end point are prescribed such that, along the centerline, the first point is equidistant from the first section start point and the first section end point.

9. The method as claimed in claim 8, wherein a distance between the first section start point and first section end point along the centerline is prescribed as a function of a maximum cross-sectional radius of the tubular structure along the centerline.

10. The method as claimed in claim 9, wherein 5 to 50 times the maximum cross-sectional radius of the tubular structure along the centerline is prescribed as the distance along the centerline between the first section start point and the first section end point.

11. The method as claimed in claim 10, wherein 20 times the maximum cross-sectional radius of the tubular structure along the centerline is prescribed as the distance along the centerline between the first section start point and the first section end point.

12. The method as claimed in claim 10, wherein 10 times the maximum cross-sectional radius of the tubular structure along the centerline is prescribed as the distance along the centerline between the first section start point and the first section end point.

13. The method as claimed in claim 2, wherein a distance between the first section start point and first section end point along the centerline is prescribed as a function of a maximum cross-sectional radius of the tubular structure along the centerline.

14. The method as claimed in claim 13, wherein 5 to 50 times the maximum cross-sectional radius of the tubular structure along the centerline is prescribed as the distance along the centerline between the first section start point and the first section end point.

15. The method as claimed in claim 14, wherein 20 times the maximum cross-sectional radius of the tubular structure along the centerline is prescribed as the distance along the centerline between the first section start point and the first section end point.

16. The method as claimed in claim 14, wherein 10 times the maximum cross-sectional radius of the tubular structure along the centerline is prescribed as the distance along the centerline between the first section start point and the first section end point.

17. The method as claimed in claim 2, wherein the first value R is selected such that the first value R is less than or equal to a maximum cross-sectional radius of the tubular structure along the first section.

18. The method as claimed in claim 17, wherein the first value R is less than or equal to half the maximum cross-sectional radius.

19. The method of claim 2, wherein the tubular anatomical structure is a vessel structure.

20. A computer readable medium including program segments for, when executed on a computer device, causing the computer device to implement the method of claim 2.

21. A method for visualizing tubular anatomical structures in medical 3D image records, comprising:
providing 3D image data of a tubular anatomical structure;
determining a centerline of the tubular anatomical structure in the 3D image data;
selecting a point of the determined centerline;
generating a 2D slice image assigned to the selected point, the 2D slice image representing a sectional plane in the 3D image data, the sectional plane being arranged relative to a section of the centerline, the section including the point, a prescribable section start point and a section end point of the section, such that an orthogonal distance from the sectional plane for each centerline point of the section is less than or equal to a prescribed value R, R being selected to be relatively greater than a value $R_{krit}$ and $R_{krit}$ specifying a value of R for which precisely one such sectional plane is determinable; and
visually displaying the generated 2D slice image,
wherein the generating a 2D slice image includes generating a 2D cross section assigned to the point,
the visually displaying the generated 2D slice image includes visually displaying the 2D cross section, and
the 2D cross section represents a sectional plane in the 3D image data which is aligned orthogonally with respect to the centerline of the tubular structure at the point.

22. The method as claimed in claim 21, wherein the generating a 2D slice image includes generating, two 2D slice images and the 2D cross section for the point.

23. The method as claimed in claim 22, wherein sectional planes of the two 2D slice images and the 2D cross section in the 3D image data are arranged orthogonally with respect to one another.

24. An apparatus for visualizing tubular anatomical structures from medical 3D image records, comprising:
a storage module to store 3D image data of a tubular anatomical structure;
a first module to determine a centerline of the tubular anatomical structure based on the 3D image data;
a second module to select a point on the determined centerline;
a third module to generate a 2D slice image assigned to the selected point from the 3D image data, the 2D slice image representing a sectional plane in the 3D image data, the sectional plane being arranged relative to a section of the centerline, the section including the point, a prescribable section start point, and a section end point of the section, such that an orthogonal distance from the sectional plane for each centerline point of the section is less than or equal to a prescribed value R, R being selected to be relatively greater than a value $R_{krit}$, and $R_{krit}$ specifying the value of R for which precisely one such sectional plane is determinable; and
a display unit to visually display the generated 2D slice image assigned to the position,
wherein the third module is configured to effect a principal component analysis of all centerline points of the section to determine a 3D orientation of the sectional plane, the 3D orientation being defined by two vectors which represent the relatively largest and relatively second-largest spatial variance of the centerline points of the section.

25. An apparatus for visualizing tubular anatomical structures from medical 3D image records, comprising:
a storage module to store 3D image data of a tubular anatomical structure;
a first module to determine a centerline of the tubular anatomical structure based on the 3D image data;

a second module to select first and second points on the determined centerline;

a third module to generate a first 2D slice image assigned to the first point from the 3D image data, the 2D slice image representing a first sectional plane in the 3D image data, the first sectional plane being arranged relative to a section of the centerline, the section including the first point, a prescribable section start point, and a section end point of the section, such that an orthogonal distance from the first sectional plane for each centerline point of the section is less than or equal to a prescribed value R, the value R being selected to be relatively greater than a value $R_{krit}$, and the value $R_{krit}$ specifying a value of R for which precisely one such first sectional plane is determinable, and generate a second 2D slice image assigned to the second point, the second 2D slice image representing a second sectional plane in the 3D image data; and a display unit to visually display the first and second 2D slice images, wherein the third module is configured to perform a quality measure dependent optimization method for determining a 3D orientation of the second sectional plane in which an angle $\alpha$ between a first normal of a first 2D sectional plane and a second normal of a second 2D sectional plane is used as a quality measure, the first normal of the first 2D sectional plane relating to the first 2D slice image and the second normal of the second 2D sectional plane relating to the second 2D slice image, and determine the 3D orientation of the second sectional plane such that the angle $\alpha$ is minimized.

26. The apparatus as claimed in claim 25, wherein the third module is configured to automatically prescribe at least one of the section start point and the section end point as a function of the first point, of R and of $R_{krit}$.

\* \* \* \* \*